(12) United States Patent
Tsudera et al.

(10) Patent No.: US 7,112,691 B2
(45) Date of Patent: Sep. 26, 2006

(54) PURIFICATION METHOD FOR ORGANOMETALLIC COMPOUNDS AND ORGANOMETALLIC COMPOUNDS OBTAINED THEREFROM

(75) Inventors: Takanobu Tsudera, Joetsu (JP); Daisuke Iwai, Joetsu (JP); Takayuki Honma, Joetsu (JP); Hiromi Nishiwaki, Joetsu (JP); Shuji Tanaka, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 11/154,534

(22) Filed: Jun. 17, 2005

(65) Prior Publication Data

US 2005/0283015 A1    Dec. 22, 2005

(30) Foreign Application Priority Data

Jun. 18, 2004  (JP)  ............................. 2004-180971

(51) Int. Cl.
*C07F 5/06*  (2006.01)
*C07F 3/00*  (2006.01)
*C07F 5/00*  (2006.01)

(52) U.S. Cl. .................. 556/187; 556/1; 556/121; 556/170

(58) Field of Classification Search ................ 556/170, 556/187, 1, 121
See application file for complete search history.

(56) References Cited

U.S. PATENT DOCUMENTS

| 4,720,561 A | 1/1988 | Bradley et al. |
| 4,797,500 A * | 1/1989 | Kadokura et al. ............. 556/1 |
| 4,847,399 A * | 7/1989 | Hallock et al. ............... 556/1 |
| 6,482,968 B1 | 11/2002 | Tran et al. |
| 2004/0254389 A1* | 12/2004 | Odedra et al. ................ 556/1 |
| 2004/0260106 A1* | 12/2004 | Honma et al. ................ 556/1 |
| 2005/0004383 A1* | 1/2005 | Nishiwaki et al. ............ 556/1 |

FOREIGN PATENT DOCUMENTS

| EP | 0 116 319 A2 | 8/1984 |
| GB | 2 183 651 A | 6/1987 |
| JP | 62-132888 | 6/1987 |
| JP | 62-185090 | 8/1987 |
| JP | 5-35154 | 5/1993 |
| JP | 6-145177 | 5/1994 |
| JP | 8-12678 | 1/1996 |
| JP | 20003-518007 | 6/2003 |
| WO | WO 00/71551 A2 | 11/2000 |

* cited by examiner

*Primary Examiner*—Porfirio Nazario-Gonzalez
(74) *Attorney, Agent, or Firm*—Westerman, Hattori, Daniels & Adrian, LLP.

(57) ABSTRACT

A method of purifying an organometallic compound comprising
distilling the organometallic compound for purification while blowing an inert gas through a vapor of the organopolysiloxane, thereby removing from the organometallic compound an impurity having a higher vapor pressure than the organometallic compound.

7 Claims, No Drawings

PURIFICATION METHOD FOR ORGANOMETALLIC COMPOUNDS AND ORGANOMETALLIC COMPOUNDS OBTAINED THEREFROM

CROSS-REFERENCE TO RELATED APPLICATION

This non-provisional application claims priority under 35 U.S.C. §119(a) on Patent Application No. 2004-180971 filed in Japan on Jun. 18, 2004, the entire contents of which are hereby incorporated by reference.

BACKGROUND OF THE INVENTION

This invention relates to a purification method for organometallic compounds, especially trimethylaluminum. More specifically, this invention is concerned with a method for lowering the concentration of an impurity, especially an organosilicon compound, which is contained in an organometallic compound such as trimethylaluminum effectively used for the production of a compound semiconductor and has a higher vapor pressure than the organometallic compound. This invention is also concerned with a purified organometallic compound obtained by the purification method.

Compound semiconductor materials such as gallium arsenide, indium phosphide and gallium phosphide are well known materials having uses in electronics industry in such applications as microwave oscillators, semiconductor light-emitting diodes, lasers and infrared detectors. The quality of a compound semiconductor available from an epitaxial growth of an organometallic compound is significantly controlled by impurities in the organometallic compound as a raw material. Therefor, high purity is required for the organometallic compound to obtain the compound semiconductor material with a high function.

Typical examples of organometallic compounds used in the production of compound semiconductors include trimethylgallium, trimethylindium, and trimethylaluminum. Among these, trimethylgallium and trimethylindium are produced from gallium chloride and trimethylaluminum and from indium chloride and trimethylaluminum, respectively, and the purities of trimethylgallium and trimethylindium are considered to depend on the purity of trimethylaluminum as their starting material. It is, accordingly, the most important step in the production of these organometallic compounds to highly purify trimethylaluminum.

The impurities in an organometallic compound to be purified include hydrocarbon compounds and in addition, organometallic compounds and metallic compounds containing metals different from the metal in the organometallic compound to be purified. Among these impurities, those having higher or similar vapor pressures compared with the organometallic compound to be purified may form impurity inclusions in a compound semiconductor to be produced from the purified organometallic compound if they still remain even after the purification, and therefore, are considered to be particularly harmful.

Among impurities having high vapor pressures, organosilicon components with Group IV metals contained therein are desired to be removed completely, because they lower electrical properties and optical properties of Group III-V compound semiconductors such as gallium arsenide if they are included in the compound semiconductors.

As processes for removing impurities having high vapor pressures, there have heretofore been reported adduct purification processes (JP-B 5-35154 and JP-A 62-185090), processes involving distillation in contact with metallic sodium or metallic potassium (JP-A 62-132888 and JP-A 8-12678), and processes for purifying liquid organometallic compounds by cooling and solidifying them (JP-A 2003-518007).

However, the adduct purification processes and the processes involving distillation in contact with metallic sodium or metallic potassium are accompanied by many drawbacks in that, as they require the addition of a solvent and the chemical for the treatment to an organometallic compound to be pured, the purity of the solvent and chemical need to be made very high before their addition, the solvent and chemical have to be treated after use, the solvent and chemical is costly, and the handling of the solvent and chemical is dangerous. The purification processes involving cooling and solidification of organometallic compounds also have problems in that applicable organometallic compounds are limited and the removal of impurities is insufficient.

SUMMARY OF THE INVENTION

It is an object of the present invention, therefore, to provide a purification method for an organometallic compound, which can industrially and easily remove impurities of high vapor pressures at high efficiency from the organometallic compound without practically using any additive and also to provide a purified organometallic compound obtained by the method.

To achieve the above-described objects, the present inventors have proceeded with an extensive investigation. As a result, it has been found that blowing of an inert gas through a vapor of an organometallic compound during distillation purification thereof makes it possible to effectively remove impurities having higher vapor pressures than the organometallic compound and to achieve the above-described objects by an industrially easy process without using any additive, leading to the completion of the present invention.

In one aspect of the present invention, there is thus provided a method of purifying an organometallic compound comprising distilling the organometallic compound for purification while blowing an inert gas through a vapor of the organometallic compound, thereby removing from the organometallic compound an impurity having a higher vapor pressure than the organometallic compound. The organometallic compound is preferably trimethylaluminum. The impurity may be an organosilicon compound having a higher vapor pressure than the organometallic compound. In another aspect of the present invention, there is also provided an organometallic compound obtained by the above-described purification method and containing 1 ppm or lower of an organosilicon compound having a higher vapor pressure than the organometallic compound.

The process of the present invention can bring about an industrial advantage that impurities of high vapor pressures in an organometallic compound can be removed easily at high efficiency. Further, an epitaxial growth of the highly-purified organometallic compound can produce a high-quality compound semiconductor.

DETAILED DESCRIPTION OF THE PREFERRED EMBODIMENTS

The method of purifying an organometallic compound according to the present invention comprises a method of purifying an organometallic compound comprising distilling the organometallic compound for purification while blowing an inert gas through a vapor of the organometallic compound, thereby removing from the organometallic compound an impurity having a higher vapor pressure than the organometallic compound.

Examples of the organometallic compound which is purified by the process of the present invention include trimethylaluminum, trimethylgallium, triethylgallium, triethylaluminum, trimethylindium, dimethylzinc, diethylzinc, bis(cyclopentadienyl)magnesium, and bis(methylcyclopentadienyl)magnesium.

On the other hand, examples of the impurity—which is contained in the organometallic compound, has a high vapor pressure and is to be removed from the organometallic compound—include organometallic compounds containing Ca, Cd, Cr, Cu, Fe, Mg, Mn, Si or Zn different from the metal in the organometallic compound to be purified, and low boiling point hydrocarbon compounds having 1 to 9 carbon atoms, especially organosilicon compounds such as tetramethylsilane, trimethylchlorosilane, tetrachlorosilane, methyltrichlorosilane, ethyltrimethylsilane, dimethylethylchlorosilane, diethylmethylchlorosilane, dimethyldiethylsilane, ethyltrichlorosilane, triethylmethylsilane, diethyldichlorosilane, triethylchlorosilane, and tetraethylsilane.

It is to be noted that in the case of trimethylaluminum, for example, such organosilicon compounds are included therein as a result of the change of metallic silicon containing in metallic aluminum into the organosilicon compounds through chemical reactions during the production steps of trimethylaluminum, and that these organosilicon components are generally contained in an amount of about 10 to 200 ppm in total in trimethylaluminum before their purification but the concentration of the organosilicon components can be lowered to 1 ppm or less by the process of the present invention. It is also to be noted that the term "the concentration of the organosilicon components" means the concentration of Si in the organosilicon compound as an impurity.

Further, impurities having low vapor pressures in the organometallic compounds such as metallic compounds, trialuminum oxide, high boiling point hydrocarbon components having 10 or more carbon atoms, and the like can also be removed by distillation.

Upon subjecting the organometallic compound to distillation purification, an inert gas is blown through a vapor of the organometallic compound. Examples of gases used as inert gases in the present invention include helium, argon, nitrogen, hydrogen, or a mixture thereof. The inert gases can be used either singly or in combination. It is desired to use them in a form highly purified by lowering the concentrations of oxygen and water.

The blow rate of the inert gas can be 50% by volume or lower, preferably from 1 to 10% by volume based on the vapor of the organometallic compound. A blow rate lower than 1% by volume is not fully effective for the removal of impurities, while a blow rate higher than 50% by volume has a problem that the recovery rate of the organometallic compound may be lowered.

The inert gas can be introduced at any place where the vapor of the organometallic compound exists, such as a still pot, column, purification tube or condenser. The inert gas can be introduced at any one of total reflux, pre-distillation, main distillation and post-distillation, or during the distillation. It is usually sufficient to conduct the distillation purification only once. The distillation purification may, however, be repeated several times as needed.

EXAMPLES

Examples and Comparative Examples of the invention are given below by way of illustration and not by way of limitation. It is to be noted that the concentration of organosilicon components in the organometallic compounds of the following Examples was determined based on the quantitation by inductively-coupled plasma emission spectrometry subsequent to their extraction in a hydrocarbon solvent.

Example 1

A 1,000-mL SUS vessel equipped with a reflux condenser and a 40-tray distillation column was fully purged with helium, and then trimethylaluminum (497 g) was charged in the vessel. While introducing high-purity helium at 100 mL/min, distillation purification was conducted at 127° C. under environmental pressure to afford a main distillate (347 g). As a result of measurement of the concentration of organosilicon components, it was found that the concentration had been lowered to 0.7 ppm after the purification as opposed to 173 ppm before the purification.

Example 2

Trimethylaluminum was purified in a similar manner as in Example 1 except that the concentration of organosilicon components in trimethylaluminum before the purification was 24.5 ppm and the blow rate of high-purity helium was set at 50 mL/min. As a result of measurement of the concentration of organosilicon components in trimethylaluminum after the purification, the concentration was found to be 0.2 ppm.

Example 3

Trimethylaluminum was purified in a similar manner as in Example 2 except that the concentration of organosilicon components in trimethylaluminum before the purification was 25.3 ppm. As a result of measurement of the concentration of organosilicon components in trimethylaluminum after the purification, the concentration was found to be 0.08 ppm.

Comparative Example 1

Trimethylaluminum was purified in a similar manner as in Example 1 except that high-purity helium was not blown. As a result of measurement of the concentration of organosilicon components in the trimethylaluminum after the purification, the concentration was found to be 9.4 ppm.

Comparative Example 2

Trimethylaluminum was purified in a similar manner as in Example 2 except that high-purity helium was not blown. As a result of measurement of the concentration of organosilicon components in trimethylaluminum after the purification, the concentration was found to be 0.7 ppm.

Comparative Example 3

Trimethylaluminum was purified in a similar manner as in Example 3 except that high-purity helium was not blown. As a result of measurement of the concentration of organosilicon components in trimethylaluminum after the purification, the concentration was found to be 0.4 ppm.

Japanese Patent Application No. 2004-180971 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A method of purifying an organometallic compound comprising distilling the organometallic compound for purification while blowing an inert gas through a vapor of the organometallic compound, thereby removing from the organometallic compound an impurity having a higher vapor pressure than the organometallic compound.

2. The method of claim 1, wherein the organometallic compound is trimethylaluminum.

3. The method of claim 1, wherein the impurity is an organosilicon compound having a higher vapor pressure than the organometallic compound.

4. The method of claim 1, wherein the inert gas is helium, argon, nitrogen, hydrogen or a mixture thereof.

5. The method of claim 1, wherein the blow rate of the inert gas is 50% by volume or lower based on the vapor of the organometallic compound.

6. The method of claim 1, wherein the organometallic compound is one selected from the group consisting of trimethylaluminum, trimethylgallium, triethylgallium, triethylaluminum, trimethylindium, dimethylzinc, diethylzinc, bis(cyclopentadienyl)magnesium, and bis(methylcyclopentadienyl)magnesium.

7. The method of claim 1, wherein the impurity is an organometallic impurity compound containing Ca, Cd, Cr, Cu, Fe, Mg, Mn, Si, or Zn different from a metal in the organometallic compound to be purified, and a low boiling point hydrocarbon compound having 1 to 9 carbon atoms.

* * * * *